(12) United States Patent
Oh et al.

(10) Patent No.: US 11,638,519 B2
(45) Date of Patent: May 2, 2023

(54) SYSTEMS AND METHODS FOR TREATING PROSTATE DISORDERS

(71) Applicant: SEOUL NATIONAL UNIVERSITY HOSPITAL, Seoul (KR)

(72) Inventors: Seung-June Oh, Seoul (KR); Hyoun-Joong Kong, Seoul (KR)

(73) Assignee: SEOUL NATIONAL UNIVERSITY HOSPITAL, Seoul (KR)

( * ) Notice: Subject to any disclaimer, the term of this patent is extended or adjusted under 35 U.S.C. 154(b) by 428 days.

(21) Appl. No.: 16/997,931

(22) Filed: Aug. 19, 2020

(65) Prior Publication Data

US 2020/0375449 A1 Dec. 3, 2020

Related U.S. Application Data

(62) Division of application No. 16/010,483, filed on Jun. 17, 2018, now Pat. No. 10,786,147.

(Continued)

(51) Int. Cl.
*A61B 17/32* (2006.01)
*A61B 1/307* (2006.01)
(Continued)

(52) U.S. Cl.
CPC ............ *A61B 1/307* (2013.01); *A61B 1/0002* (2013.01); *A61B 1/0005* (2013.01); *A61B 1/00006* (2013.01); *A61B 1/00045* (2013.01); *A61B 1/00055* (2013.01); *A61B 1/00091* (2013.01); *A61B 1/00094* (2013.01); *A61B 1/00096* (2013.01); *A61B 1/00135* (2013.01); *A61B 1/015* (2013.01); *A61B 1/018* (2013.01); *A61B 8/0833* (2013.01); *A61B 8/4209* (2013.01); *A61B 17/32002* (2013.01); *A61B 1/042* (2013.01); *A61B 1/0669* (2013.01); *A61B 1/07* (2013.01); *A61B 2017/00017* (2013.01); *A61B 2017/00119* (2013.01);

(Continued)

(58) Field of Classification Search
CPC ... A61B 17/32; A61B 17/32002; A61B 17/29; A61B 17/320016; A61B 2017/320024; A61B 2017/00017; A61B 2017/00119; A61B 2017/00274
See application file for complete search history.

(56) References Cited

U.S. PATENT DOCUMENTS

| | | | |
|---|---|---|---|
| 7,981,073 B2* | 7/2011 | Mollstam | A61B 1/015 604/118 |
| 2013/0006231 A1* | 1/2013 | Sharma | A61B 18/04 606/27 |
| 2017/0042504 A1* | 2/2017 | Rich | A61B 8/0883 |

* cited by examiner

*Primary Examiner* — Vi X Nguyen
(74) *Attorney, Agent, or Firm* — Han's Law Office

(57) ABSTRACT

A system for monitoring a volume of a bladder during a surgical procedure. The system includes one or more processors; and a memory that is communicatively coupled to the one or more processors and stores one or more sequences of instructions, which when executed by one or more processors causes steps to be performed comprising: receiving information of a maximum volume of the bladder before the surgical procedure; receiving one or more ultrasound images from an ultrasonic scanner; based on the one or more ultrasound images, determining a volume of the bladder; comparing a maximum volume of the bladder to the determined volume of the bladder; and responsive to a difference between the maximum volume and determine volume of the bladder exceeding a threshold, issuing a warning associated with the difference.

4 Claims, 11 Drawing Sheets

Related U.S. Application Data

(60) Provisional application No. 62/636,116, filed on Feb. 27, 2018.

(51) Int. Cl.
    *A61B 1/00*     (2006.01)
    *A61B 8/08*     (2006.01)
    *A61B 8/00*     (2006.01)
    *A61B 1/018*     (2006.01)
    *A61B 1/015*     (2006.01)
    *A61B 1/07*     (2006.01)
    *A61B 90/00*     (2016.01)
    *A61B 1/04*     (2006.01)
    *A61B 1/06*     (2006.01)
    *A61B 17/00*     (2006.01)

(52) U.S. Cl.
    CPC ........ *A61B 2017/00274* (2013.01); *A61B 2017/320024* (2013.01); *A61B 2090/061* (2016.02); *A61B 2090/063* (2016.02); *A61B 2090/064* (2016.02); *A61B 2217/005* (2013.01); *A61B 2217/007* (2013.01); *A61B 2562/0247* (2013.01)

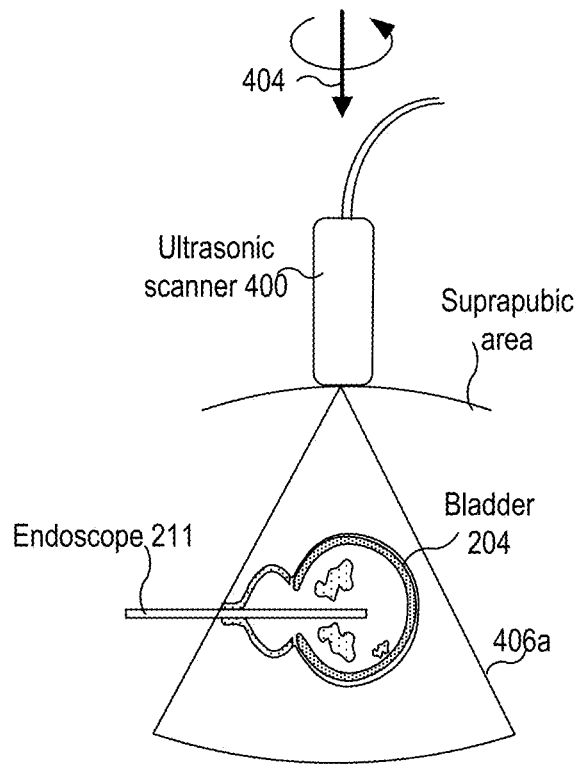
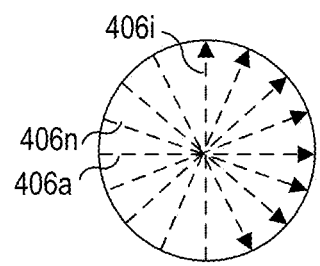
FIG. 4A
FIG. 4B
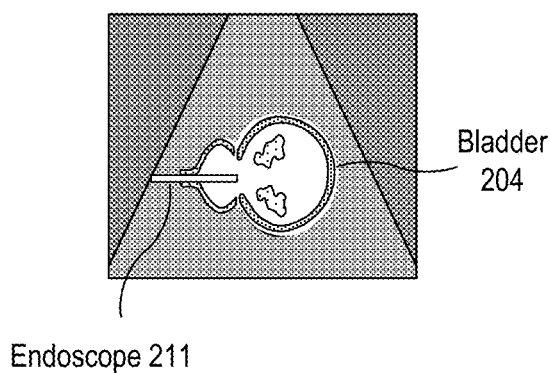
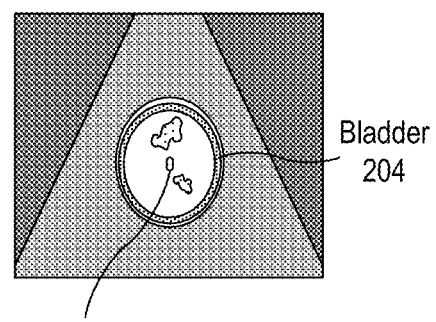
FIG. 4C
FIG. 4D

| Signals involved | Scenario 1 | Scenario 2 | Scenario 3 | Scenario 4 |
|---|---|---|---|---|
| Inflow-side pressure sensor 215 | High (>60 cm H2O) | Moderate (20 - 40 cm H2O) | Low (<20 cm H2O) | Low (<20 cm H2O) |
| Outflow-side pressure sensor 219 | High (>60 cm H2O) | Moderate (20 - 40 cm H2O) | Low (<20 cm H2O) | Low (<20 cm H2O) |
| Pressure sensor 804 at morcellator tip | High (>60 cm H2O) | Moderate (20 - 40 cm H2O) | Low (+20 cm H2O) | Low (<20 cm H2O) |
| Distance sensor 609 at morcellator tip | Far (>5cm) | Far (>5cm) | Near (<3cm) | Near (<3cm) |
| Ultrasound 218 - measured bladder volume 233 and image 230 | Full (>500ml) | Full (>500ml) | Collapsed (<200ml) | Collapsed (<200ml) |
| Flow meter 214 at the irrigation tube 213 | Normal flow (++) | Normal flow (++) | Normal flow (++) | Low flow (+) or Zero |
| Diagnosis | OK | Normal (during morcellation) | Excessive outflow (outflow inadvertently opened and/or suctioning-out too much) | Low inflow (inflow obstructed and/or irrigation fluid depleted) |

FIG. 11

SYSTEMS AND METHODS FOR TREATING PROSTATE DISORDERS

CROSS-REFERENCE TO PRIOR APPLICATIONS

This application is a divisional application of a U.S. patent application Ser. No. 16/010,483, filed on Jun. 17, 2018, entitled "Treating Prostate Disorders," which claims priority of U.S. Patent Application No. 62/636,116, filed on Feb. 27, 2018, entitled "Treating Prostate Disorders," which are hereby incorporated by reference in their entirety.

TECHNICAL FIELD

The present invention relates to systems and methods for the treatment of prostatic disorders in men, more specifically, systems and methods for treating benign prostatic hyperplasia (BPH) using minimally invasive tools.

DESCRIPTION OF THE RELATED ART

The prostate is a gland surrounding the bladder neck and proximal urethra in men and releasing prostatic fluid. Benign prostatic hyperplasia (BPH), which consists of prostatic adenoma, is a noncancerous enlargement of the prostate and is common prostate condition in older men. It causes bladder outflow obstruction and lower urinary tract symptoms including voiding and storage symptoms. It can also cause dysfunction of the urinary bladder (hereinafter, shortly bladder), or kidney damage.

Traditionally, transurethral resection of prostate (TURP) has been considered as the gold standard transurethral surgery for treating BPH. Recently, several other surgical procedures, such as KTP laser vaporization, bipolar electrosurgery, Thulium laser enucleation, and Holmium laser enucleation of prostate (HoLEP) have been developed and have been popularized. Some of these newly developed procedures adopting enucleation technique may separate prostatic adenomas from the prostate, leaving only prostatic capsule. Large prostatic adenomas can be moved to the bladder cavity for later transurethral retrieval after they are cut into smaller pieces enough for them to be passed through the urethral lumen. For instance, HoLEP procedure, which is a minimally invasive surgical procedure for BPH, consists of two independent phases: enucleation of prostatic adenoma and subsequent morcellation of enucleated adenoma tissue(s). FIGS. 1A-1C illustrate the first phase of the conventional HoLEP procedure, where the prostatic adenoma 110 that was enlarged due to BPH and blocking the flow of urine out of the bladder 100 is enucleated. (In FIG. 1A, the dotted area 102 is collectively referred to as prostate, where the prostate was enlarged due to BPH.) Typically, with the patient under general or spinal anesthesia, the surgeon inserts a resectoscope working element 109 combined with an endoscope sheath into the patient's body through the urethra. The operator uses the laser beam 108 emitting from the tip of the laser fiber accommodated in the resectoscope working element to enucleate the prostatic adenoma 110 from the prostate capsule 103, leaving just the capsule 103 in place. The surgeon pushes the separated pieces of prostatic adenoma 110 into the bladder 100 so that the pieces of enucleated prostatic adenoma 104 are placed in the bladder 100. In general, the pieces of enucleated prostatic adenoma is too big to pass through the urethra. Thus, to remove the pieces of enucleated prostatic adenoma 104 from the bladder, the surgeon inserts a morcellation device through the sheath of the endoscope into the patient's bladder, fragments the pieces of enucleated prostatic adenoma 104 and sucks the smaller tissue from the bladder 100 through a tube that is a part of the morcellation device.

Typically, the morcellation device is engaged into an endoscope. Also, the tip portion of the endoscope inserted into the patient bladder has a light source and a camera lens so that the surgeon can visually locate the pieces of enucleated prostatic adenoma 104 and the tip portion of the morcellation device during the procedure. One of the most significant dangers associated with the morcellation procedure is that the inner pressure of the bladder 100 may unexpectedly drop during the procedure, causing the bladder 100 to collapse. If the bladder shrinks, the tip of the morcellator may inadvertently touch and damage the inner wall of the bladder 100 with the sharp blade of the morcellation device, causing accidental perforation on the bladder wall 100. Thus, it is important to ensure that the bladder remains fully distended during the procedure and to maintain a safe distance between the blade of the morcellation device and the bladder inner wall.

In the conventional morcellation procedure, an assistant has to continuously monitor the bladder distention by frequent manual palpation and notify the operating surgeon if the bladder is not full. Typically, during the procedure, the assistant palpate the patient's suprapubic area with a hand(s) at preset time intervals and, based on the sensation at the hand(s), determines whether the bladder is full or not. However, for obese patients or patients with small bladder, this technique may not provide accurate information of the bladder distention status due to the abdominal fat layer between the assistant's finger and the bladder. Also, if the assistant is not sufficiently experienced, he may not be able to determine the bladder status correctly, failing to properly report the bladder status to the operating surgeon.

During the morcellation phase of the surgery, the bladder may collapse for several reasons: the irrigation fluid container becomes empty, the tube from the irrigation fluid container to the bladder becomes blocked, the valve in the upstream side of the bladder becomes inadvertently closed, the valve on the downstream side of the bladder becomes inadvertently open, so on. In general, several assistants in the operation room need to carefully and continuously monitor the entire flow system to ensure that the bladder remains fully distended. As such, there is a need for systems and methods for real-time monitoring the bladder status during the BPH surgery and maintain a safe distance between the bladder inner wall and morcellation device to thereby obviate the inadvertent damages to the bladder while the work load on the assistants is reduced during the BPH surgery.

SUMMARY OF DISCLOSURE

In embodiments, a system for real-time controlling a pressure inside a bladder through an endoscope includes one or more processors and a memory that is communicatively coupled to the one or more processors. The distal end portion of the endoscope is configured to be located inside the bladder. The endoscope has an inlet port that is configured to allow fluid to enter the bladder through the inlet port and an outlet port that is configured to allow fluid in the bladder to exit the bladder through the outlet port. The memory stores one or more sequences of instructions, which when executed by one or more processors causes steps to be performed including: receiving a first signal from a first pressure sensor installed in a first fluid passageway that is in fluid communication with the inlet port of the endoscope; receiving a second signal from a second pressure sensor installed in a second fluid passageway that is in fluid communication with the outlet port of the endoscope; and based on at least one of the first and second signals, actuating a valve that is installed in the first fluid passageway of fluid so as to adjust a flow rate of fluid flowing into the bladder through the inlet port of the endoscope.

In embodiments, a method for real-time controlling a pressure inside a bladder through an endoscope include receiving a first signal from a first pressure sensor installed in a first fluid passageway that is in fluid communication with the inlet port of the endoscope. The distal end portion of the endoscope is configured to be located inside the bladder. The endoscope has an inlet port that is configured to allow fluid to enter the bladder through the inlet port and an outlet port that is configured to allow fluid in the bladder to exit the bladder through the outlet port. The method further includes: receiving a second signal from a second pressure sensor installed in a second fluid passageway that is in fluid communication with the outlet port of the endoscope; and based on at least one of the first and second signals, actuating a valve that is installed in the first fluid passageway of fluid so as to adjust a flow rate of fluid flowing into the bladder through the inlet port of the endoscope.

In embodiments, a system for real-time monitoring of bladder volume during a surgical procedure includes one or more processors and a memory that is communicatively coupled to the one or more processors. The memory stores one or more sequences of instructions, which when executed by one or more processors causes steps to be performed including: receiving information of a maximum volume of the bladder before the surgical procedure; receiving one or more ultrasound images from an ultrasonic scanner; based on the one or more ultrasound images, determining a volume of the bladder; comparing a maximum volume of the bladder to the determined volume of the bladder; and if a difference between the maximum volume and determine volume of the bladder exceeds a threshold, issuing a warning associated with the difference.

In embodiments, a morcellator for fragmenting a piece of tissue inside a bladder includes: a morcellation blade set having an outer blade and an inner blade that slidably engages the outer blade, the inner blade being configured to fragment a piece of tissue by reciprocating, oscillating or rotating relative to the outer blade; and a distance sensor disposed on the outer blade and configure to measure the distance between the outer blade and an inner wall of a bladder.

BRIEF DESCRIPTION OF THE DRAWINGS

References will be made to embodiments of the invention, examples of which may be illustrated in the accompanying figures. These figures are intended to be illustrative, not limiting. Although the invention is generally described in the context of these embodiments, it should be understood that it is not intended to limit the scope of the invention to these particular embodiments.

FIG. 4A shows a schematic diagram of an ultrasonic scanner according to embodiments of the present disclosure.

FIG. 4B shows the orientations of planes along which the ultrasonic scanner in FIG. 4A acquires two-dimensional images of the bladder according to embodiments of the present disclosure.

FIG. 4C shows an exemplary real-time ultrasonic image generated by the ultrasonic scanner in FIG. 4A according to embodiments of the present disclosure.

FIG. 4D shows an exemplary real-time ultrasonic image generated by the ultrasonic scanner in FIG. 4A according to embodiments of the present disclosure.

FIG. 11 shows a diagnosis table according to embodiments of the present disclosure.

DETAILED DESCRIPTION OF THE PREFERRED EMBODIMENTS

In the following description, for purposes of explanation, specific details are set forth in order to provide an understanding of the invention. It will be apparent, however, to one skilled in the art that the invention can be practiced without these details. Furthermore, one skilled in the art will recognize that embodiments of the present invention, described below, may be implemented in a variety of ways, such as a process, an apparatus, a system, a device, or a method on a tangible computer-readable medium.

Components shown in diagrams are illustrative of exemplary embodiments of the invention and are meant to avoid obscuring the invention. It shall also be understood that throughout this discussion that components may be described as separate functional units, which may comprise sub-units, but those skilled in the art will recognize that various components, or portions thereof, may be divided into separate components or may be integrated together, including integrated within a single system or component. It should be noted that functions or operations discussed herein may be implemented as components that may be implemented in software, hardware, or a combination thereof.

It shall also be noted that the terms "coupled" "connected" or "communicatively coupled" shall be understood to include direct connections, indirect connections through one or more intermediary devices, and wireless connections.

Furthermore, one skilled in the art shall recognize: (1) that certain steps may optionally be performed; (2) that steps may not be limited to the specific order set forth herein; and (3) that certain steps may be performed in different orders, including being done contemporaneously.

Reference in the specification to "one embodiment," "preferred embodiment," "an embodiment," or "embodiments" means that a particular feature, structure, characteristic, or function described in connection with the embodiment is included in at least one embodiment of the invention and may be in more than one embodiment. The appearances of the phrases "in one embodiment," "in an embodiment," or "in embodiments" in various places in the specification are not necessarily all referring to the same embodiment or embodiments.

Figure 1C:
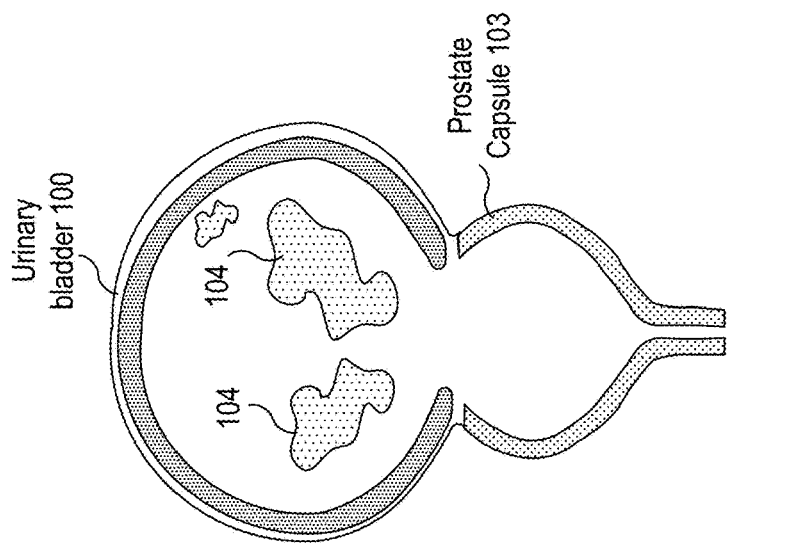
FIGS. 1A-1C illustrate the conventional HoLEP procedure that enucleates prostatic adenoma.
Figure 1B:
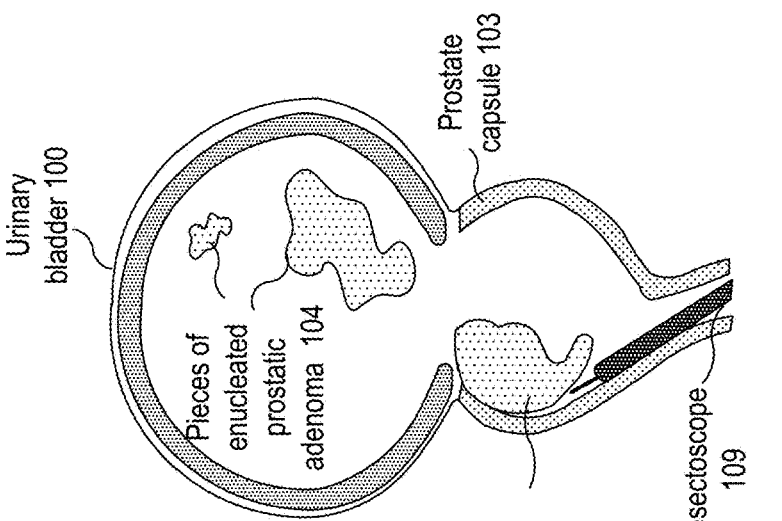
Figure 1A:
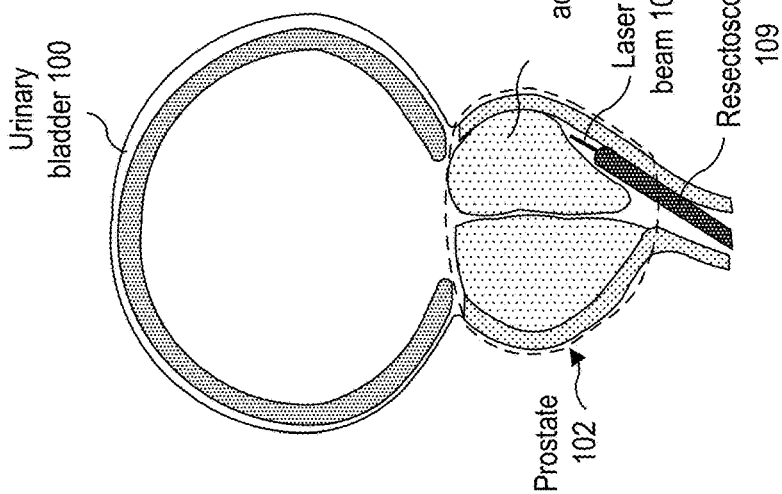
Figure 2:
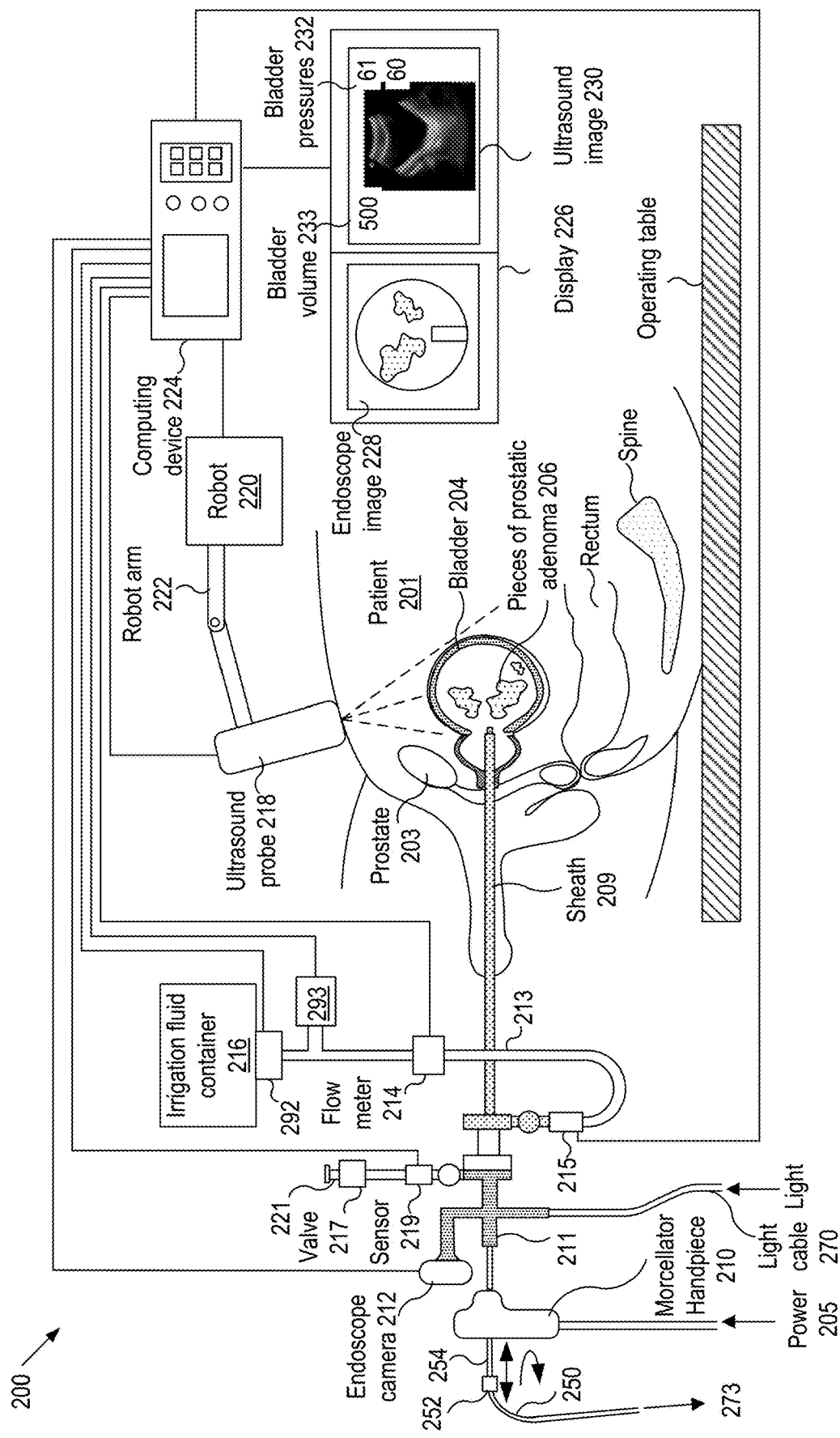
FIG. 2 shows a schematic diagram of a system for morcellation after enucleation of prostatic adenoma in patients with benign prostatic hyperplasia (BPH) according to embodiments of the present disclosure.
Figure 5:
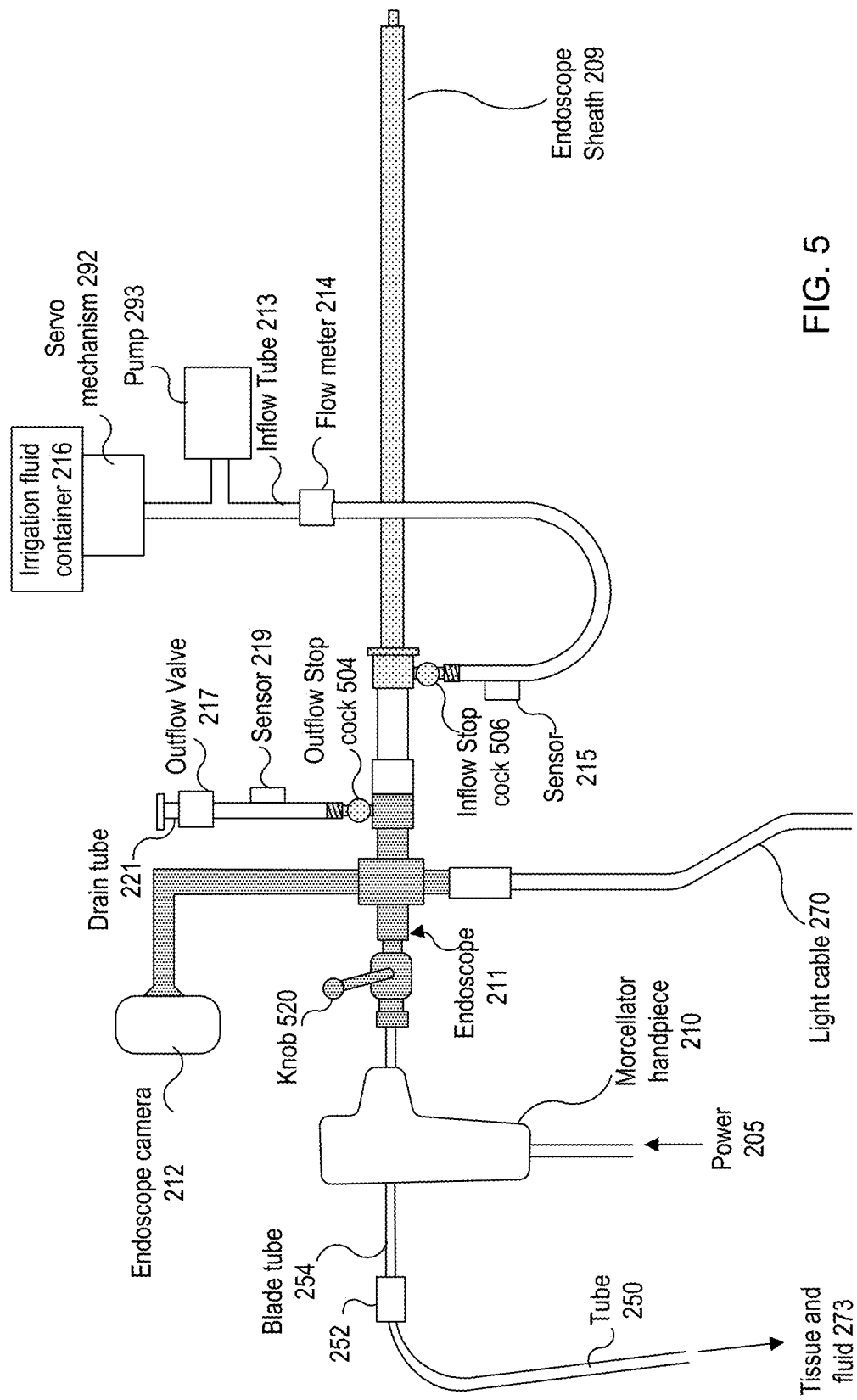
FIG. 5 shows an enlarged view of the endoscope sheath, working element and endoscope for morcellation procedure in FIG. 2 according to embodiments of the present disclosure.

FIG. 2 shows a schematic diagram of a system 200 for prostatectomy for benign prostatic hyperplasia (BPH) of a patient 201 according to embodiments of the present disclosure. FIG. 5 shows an enlarged view of the working element and endoscope for morcellation procedure in FIG. 2 according to embodiments of the present disclosure. As depicted, the system 200 may include: a computing device (or shortly device) 224 for controlling various components of the system; a display 226 having one or more screens for displaying various images, such as endoscope image 228 and ultrasound image 230 of the patient 201 on an operating table, and electrically coupled to the device 224; an ultrasound probe 218 disposed on the lower abdomen of the patient 201 and capturing ultrasound images of the bladder 204; an endoscope 211 having multiple ports for coupling various devices thereto; an endoscope sheath 209 including a slender tube that is partially inserted into the bladder 204 and prostate 203 through the urethra; an irrigation fluid container 216 for providing fluid for the bladder 204; a servo mechanism 292 secured to the irrigation fluid container 216 and operated by the computing device 224 to move in the vertical direction, to thereby adjust the hydraulic head of the fluid in the irrigation fluid container 216; and a pump 293 for injecting fluid into the bladder through the endoscope 211. (In FIGS. 2 and 5, the shaded areas correspond to the endoscope 211.) In embodiments, the ultrasound probe 218 may be attached to a control device, such as a robot arm 222, that is controlled by a robot 220. The robot 220 may be electrically coupled to and controlled by the computing device 224.

In embodiments, the endoscope 211 may accommodate various working elements. For instance, a mechanical tissue morcellation device may be engaged into the endoscope 211 and endoscope sheath 209 so that the surgeon may fragment the large pieces of enucleated prostatic adenoma (or shortly pieces of tissue) 206 in the bladder 204 into smaller pieces of tissue. FIG. 2 shows, for the purpose of illustration, a morcellation device that is engaged into the endoscope 211. However, it should be apparent to those of ordinary skill in the art that other suitable types of working elements may be engaged into the endoscope 211 and endoscope sheath 209, depending on the type of surgical procedures. In embodiments, the morcellation device (or shortly morcellator) in FIG. 2 may be used to fragment large pieces of prostatic tissue generated by various laser enucleation procedures for BPH, such as Holmium laser enucleation of prostate (HoLEP), Thulium laser, KTP laser, and, using other various enucleation procedures using energy sources including plasma or electricity.

In embodiments, the morcellation device may include: a morcellator handpiece 210 that is manipulated by the surgeon to fragment and remove the pieces of tissue 206; an inner blade 254 (which also corresponds to 806 in the FIG. 8) that reciprocates along the longitudinal axis 810 of the endoscope to fragment and remove the pieces of tissue 206; a connector 252 that connects the proximal end of the inner blade 254 (which also corresponds to 806 in FIG. 8) to a flexible tube 250. In embodiment, as described in conjunction with FIGS. 9A and 9B, the fragmented prostatic tissue in the bladder 204 may be sucked into the distal end of the inner blade 254 and exit the flexible tube 250, as indicated by an arrow 273. (Hereinafter, the term distal end refers to an end that is located inside the bladder. Likewise, the term proximal end refers to an end that is located outside the patient body and near the operating surgeon.) In embodiments, the morcellator handpiece 210 may have an electrical power line 205 that provides electrical power to drive the inner blade 254.

In embodiments, an endoscope camera 212 may be attached to the endoscope 211. As explained in conjunction with FIG. 6, a lens 604 and a visible light source 606 may be disposed at the distal end of the endoscope sheath 209 and electrically coupled to the endoscope camera 212. In embodiments, a light cable 270 may be coupled to the endoscope 211 and, in turn to the light source 606. In embodiments, the light provided through the light cable 270 may exit the light source 606 to illuminate the area nearby the distal end of the endoscope sheath 209. Using the lens 604, the endoscope camera 212 may capture the images of the pieces of tissue 206 and the tip of the morcellator, and send the captured image to the computing device 224. In embodiments, the computing device 224 may process the received image and display the endoscope image 228 on the display screen 226. In embodiments, the surgeon may manipulate the morcellator handpiece 210 while watching the endoscope image 228 during the morcellation procedure.

In embodiments, the endoscope 211 may include multiple stopcocks that regulate the fluid flow into or out of bladder. For instance, the endoscope 211 may include an inflow stopcock 506 that may be connected to the inflow tube 213 extending from the irrigation fluid container 216. As explained in conjunction with FIG. 7, the endoscope sheath 209 may be in the form of a slender tube and include an inflow passageway of the irrigation fluid that extends from the inflow stopcock 506 to the bladder 204. In embodiments, the space between the outer wall of the telescope 603 and the inner wall of the endoscope sheath 209 may form an inflow passageway through which the inflow 681 enters the bladder.

In embodiments, the endoscope 211 may include outflow stopcock 504 that may be connected to a drain tube 221. Depending on the type of procedure, the surgeon may operate the outflow stopcock 504 so that the flow rate of the fluid exiting from the bladder may be controlled. In embodiments, a flow meter 214 may be disposed on the inflow tube 213 and measure the rate of flow into the bladder 204 through the endoscope 211. In embodiments, the flow meter 214 may be electrically coupled to the computing device 224. In embodiments, the flow meter 214 may sense/detect the flow through the inflow tube 213.

It is important to monitor the bladder distention 204 continuously in real-time during the morcellation procedure so as to maintain a safe distance between the sharp blade of the morcellator and the inner wall of the bladder. In embodiments, the real-time monitoring may be performed to ensure that the bladder remains fully distended during the morcellation procedure. Since the variation in the bladder volume is closely related to the change in the pressure of the fluid inside and outside the bladder 204, the pressure of the fluid may be measured at various locations. In embodiments, one or more of three pressure sensors may be used to measure the pressure of fluid: (1) an inflow-side pressure sensor 215 to measure the pressure of fluid entering the bladder; (2) a pressure sensor (804 in FIG. 8) located near the distal end of the morcellator or distal end of endoscope sheath 209 to measure the pressure inside the bladder 204; and (3) an outflow-side pressure sensor 219 to measure the pressure of fluid exiting the bladder.

In embodiments, both the outflow stopcock 504 and the outflow valve 217 may be closed all the time during morcellation so that the fluid from the bladder may shut down during morcellation. In embodiments, during the morcellation procedure, the outflow stopcock 504 may be open and the outflow valve 217 may be closed for the outflow-side pressure sensor 219 to monitor bladder pressure. In such a case, the fluid inside the bladder 204 may exit the flexible tube 250 along with the fragmented tissue. Also, as described in conjunction with FIG. 7, the pressure measured by the outflow-side sensor 219 may indicate the pressure inside the bladder 204 if the outflow valve 217 is closed.

In embodiments, the device 224, and one or more of the sensors 215, 219, and 804 may form a system to regulate the flow into the bladder, to thereby control the bladder pressure. For instance, if the bladder pressure measured by the inflow-side sensor 215 is below a preset lower limit, a warning message, such as "bladder filling needed," may be issued to the surgeon by the speaker 312.

In embodiments, one or more of the pressures measured by the sensors 215, 219, and 804 may be displayed on the display screen 226. For instance, as shown in FIG. 2, two pressures 232 measured by the sensors 215 and 219 may be displayed on the display screen 226.

Based on the measured pressures, the computing device 224 (more specifically, the processor 302 in FIG. 3) may provide warning signals for the surgeon so that the surgeon may recognize the problem associated with the fluid flow and take proper remedial steps. For instance, if the pressure at the inflow-side sensor 215 is normal and the pressure at the outflow-side sensor 219 is too low, the computing device 224 may display a warning signal on the display 226 or provide an audio signal through the speaker 312 so that the surgeon can check if the outflow valve 217 is closed or not. In another example, if both of the pressures 232 measured by the sensors 215 and 219 are too low, the computing device 224 may issue a visual or an audio warning signal so that the surgeon can check if the inflow tube 213 or inflow stopcock 506 is blocked. Also, the computing device 224 may use the servo mechanism 292 to move the irrigation fluid container 216 instantly upward to thereby increase the hydraulic head of the fluid in the container 216 and increase the inflow rate. Alternatively, the computing device 224 may operate the pump 293 to inject fluid into the inflow tube 213.

Figure 3:
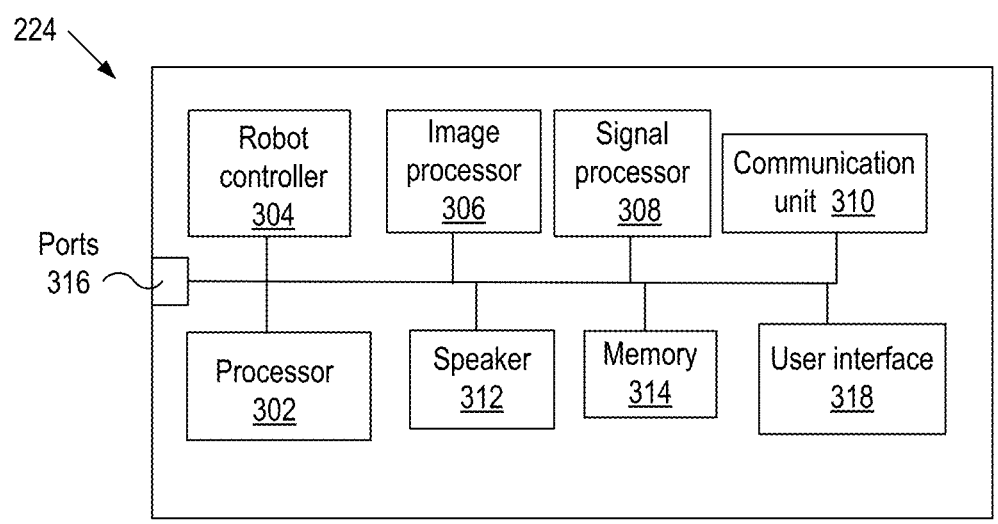
FIG. 3 shows a schematic diagram of a device for monitoring the status of bladder according to embodiments of the present disclosure.

FIG. 3 shows a schematic diagram of the computing device 224 for monitoring the status of bladder according to embodiments of the present disclosure. In embodiments, the device 224 may include: a processor 302, such as a microprocessor, for operating the components of the device as well as components connected to the device; a probe controller 304 for controlling the robot 220 and the robot arm 222 that holds the ultrasound probe 218 and capturing ultrasound images of the bladder; an image processor 306 for processing and analyzing the electrical signals received from the ultrasound probe 218 and the endoscope camera 212 and sending the processed signals to the display 226; a communication unit 310 for communicating data with various external devices, such as sensors, valve, cameras, and ultrasound probe, and forwarding the communicated signals to corresponding components of the device; a signal processor 308 for processing signals from various sensors and sending the processed signals to the display 226; a memory 314 for storing data; a speaker 312 for displaying audio signals to the surgeon/operator of the device; one or more ports 316 for accepting various terminals, such as power cable, USB, so on; and a user interface 318 for accepting input control signals from the user of the device. In embodiments, the display 226 may be included in the device 224 and located within the operation room so that the surgeon can watch the displayed images during the surgical procedures.

In embodiments, the ultrasound probe 218 may generate two-dimensional ultrasound images 230, where each image shows the sagittal view of the bladder 204 The image processor 306 may identify the morcellator tip and inner surface of the bladder in the image, and issue a warning signal when the distance between the morcellator tip and inner surface of the bladder is less than a preset safe distance. In embodiments, the warning signal may be send to the speaker 312 so that the speaker 312 may issue an audio warning signal. In embodiments, the warning signal may be sent to the display 226 so that a visual warning message may be displayed on the display screen.

As discussed above, three pressure sensors 215, 219, and 804 may be used to measure pressures of the fluid at various locations. In embodiments, the processor 302 may analyze the measured pressures to diagnose the problem associated with the fluid flow and bladder pressure, and send warning signals to the surgeon. For instance, if the pressure measured by the outflow-side sensor 219 is too low, the processor 302 may recognize that the outflow valve 217 is erroneously open and give an audio and/or visual warning signal to the surgeon through the speaker and/or display 308. In embodiments, one or more of the three pressure sensors 215, 219, and 804, and the device 224 may form a feedback loop to control the pressure inside the bladder 204.

FIG. 4A shows a schematic diagram of al ultrasonic scanner 400 according to embodiments of the present disclosure. FIG. 4B shows the orientations of planes along which the ultrasonic scanner (or equivalently ultrasound probe) 400 may acquire two-dimensional images of the bladder 204 according to embodiments of the present disclosure. In embodiments, the ultrasonic scanner 400 may correspond to the ultrasound probe 218 and be controlled by the robot arm 222 as shown in FIG. 2. In alternative embodiments, the ultrasonic scanner 400 may be a portable device that can be manually operated by a human or other suitable mechanisms.

In FIG. 4A, the plane 406a shows an exemplary cross section along which the ultrasonic scanner 400 generates a two-dimensional image of the bladder 204. In embodiments, the ultrasonic scanner 400 may be rotated by the robot arm 222 along a rotational axis 404 so that two-dimensional images are generated at preset angular intervals. In FIG. 4B, the arrows 406a-406n represents the cross sectional planes, as seen along the axis 404, along which the ultrasonic scanner takes two-dimensional images of the bladder. Based on the two-dimensional images generated by the ultrasonic scanner 400, the image processor 306 may determine the volume of the bladder 204 and the determined volume may be displayed as a number 233 on the display screen 226.

In embodiments, the surgeon may in advance input the information of the patient's bladder function, such as the frequency of urination, maximum voided volume or maximum cystometric capacity from voiding diary or urodynamic study, into the device 224 before the surgical procedure of the prostate. Based on the information, the device 224 may estimate the maximum volume of the patient's bladder. In embodiments, during the morcellation procedure, the processor 302 may compare the estimated volume with the volume 233 on the display, and send a warning signal if the difference between the two volumes exceeds a preset threshold. For instance, if the volume 233 in the display is too low compared to the volume that was estimated using the bladder information, the processor 302 may determine that the bladder is not full and issue a warning signal to the surgeon. Also, the process or 302 may operate the servo mechanism 292 to move the irrigation fluid container 216 in the vertical direction to thereby adjust the flow rate or may operate the pump 293 to inject the flow into the inflow tube 213.

FIGS. 4C and 4D show exemplary ultrasonic images generated by the scanner 400, taken along the directions 406a and 406i, respectively, according to embodiments of the present disclosure. (Figure was changed) As depicted, the image in FIG. 4C shows a sagittal view of the endoscope 211 while the image in FIG. 4D shows the cross-sectional view of the endoscope 211. As discussed above, in embodiments, the image processor 306 may identify the endoscope 211 and the inner surface of the bladder 204 in the ultrasound image and determine the distance between the tip of the endoscope 211 and the inner surface of the bladder wall 204. If the distance between the tip of the endoscope 211 and the inner surface of the bladder wall 204 is less than a preset safe distance, the image processor 306 may issue a warning signal to the surgeon.

If the surgeon prefers an image that is taken at one (e.g., 406a) of the multiple directions (or equivalently angles) 406a-406n, the surgeon may instruct the device 224 to take images along the selected direction only. For instance, the surgeon may want an image that shows a sagittal view of the endoscope 211, such as the image in FIG. 4C. In another example, the surgeon may prefer an angle at which the size of the bladder image is at its maximum. In embodiments, the device 224 may be configured to control the robot arm 222 so that the ultrasonic scanner 400 is fixed along the selected direction and produce images.

During a surgical procedure, the surgeon may change the orientation of the endoscope 211 relative to the bladder 204 while the surgeon still prefers an image that shows the side view of the endoscope 211. In embodiments, the device 224 may identify the endoscope 211 in each of multiple images taken at different angles, select an angle that shows the best sagittal view of the endoscope 211, and take images in the selected angle. In this manner, the device 224 may follow the endoscope as the surgeon moves the endoscope, continuously providing the preferred view of the endoscope 211 during the surgical procedure.

In embodiments, the image process 306 may process the ultrasound image to identify the tip portion of the endoscope sheath 209 and may trace the tip portion as the surgeon moves the endoscope sheath during the morcellation process.

Figure 6:
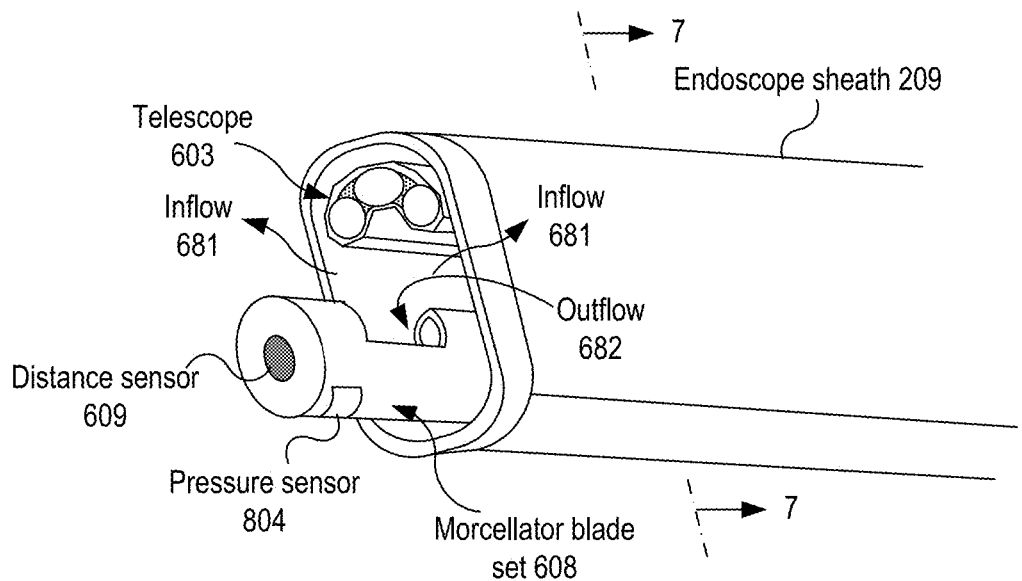
FIG. 6 shows a perspective view of a tip portion of the working element and endoscope for morcellation procedure in FIG. 5 according to embodiments of the present disclosure.
Figure 7:
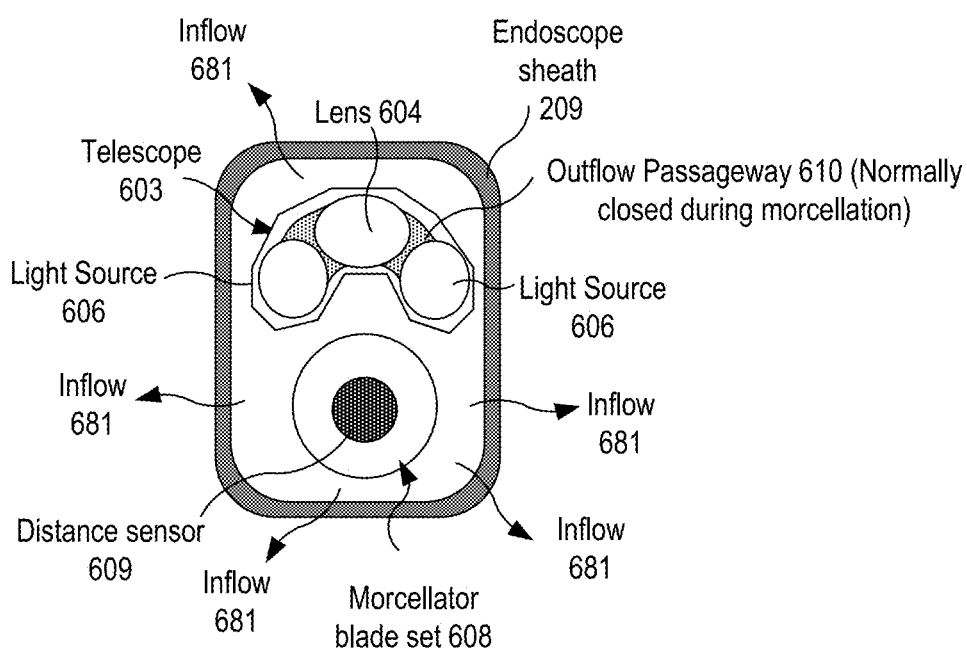
FIG. 7 shows a cross sectional view of the tip portion of the working element and endoscope for morcellation procedure in FIG. 6, taken along the direction 7-7, according to embodiments of the present disclosure.

FIG. 5 shows an enlarged view of the working element and endoscope for morcellation procedure in FIG. 2 according to embodiments of the present disclosure. FIG. 6 shows a perspective view of a tip portion of the working element and endoscope for morcellation procedure according to embodiments of the present disclosure. FIG. 7 shows a cross sectional view of the tip portion of the working element and endoscope for morcellation procedure, taken along the direction 7-7 in FIG. 6, according to embodiments of the present disclosure. As depicted, the endoscope 211 may be coupled to the endoscope sheath 209 that is inserted into urethra so that the tip portion of the endoscope sheath 209 is located inside the bladder 204.

In embodiments, the endoscope sheath 209 may be in the form of a slender tube through which various working elements and the telescopes 603 may be accommodated. In embodiments, a telescope 603 (corresponding to 211 in the FIG. 2) may be engaged through the endoscope sheath 209 and include a lens 604 and light sources 606 disposed around the lens. During the morcellation procedure, the lens 604 may continuously transmit the image of the tip portion of the morcellator blade set 608 and the prostate around the tip, where the real-time image is sent to the device 224 through the telescope 603 and the device 224 may display the real-time image 228 on the display 226. In embodiments, the endoscope 211 may include multiple stopcocks 504 and 506 for regulating the flow of fluid into or out of the bladder 204.

In embodiments, an inflow tube 213 may provide a flow passageway from an irrigation fluid container 216 to the inflow stopcock 506. When the surgeon opens the inflow stopcock 506, the irrigation fluid may enter the bladder 204 through endoscope sheath 209, as indicated by the arrows 681. In embodiments, the space between the outer wall of the telescope 603 and the endoscope sheath 209 form an inflow passageway through which the flow enters the bladder.

In embodiments, the telescope 603 may have a tubular shape and collectively refer to multiple optical elements. In embodiments, the telescope 603 may include multiple tubes thereinside, where the lens 604 and light sources 606 may be located at the proximal ends of the tubes. In embodiments, the space between the tubes and the inner wall of the telescope 603 may form an outflow passageway 610 so that the bladder is in fluid communication with the outflow stop cock 504.

In embodiments, during the morcellation procedure, the outflow valve 217 may remain closed and the outflow stopcock 504 may remain open. In such a case, since there is no fluid flow through outflow passageway 610, the pressure measured by the pressure sensor 219 may be approximately the same as the pressure at the proximal end of the outflow passageway 610. i.e., the pressure measured by the outflow-side pressure sensor 219 may be approximately the same as the pressure near the tip of the telescope 603. Also, since the tip of the telescope 603 (or endoscope sheath 209) may be located inside the bladder 204, the pressure measured by the outflow-side pressure sensor 219 may be approximately the same as the pressure inside the bladder 204.

It is noted that the endoscope 211 may have different shape and design, depending on the type or phase of surgical procedures. Also, depending on the type or phase of the surgical procedure, different working element may be engaged into the endoscope. For instance, the working element for enucleation procedure (not shown in FIG. 5) may be engaged into the endoscope 211. Upon completion of the enucleation procedure, the surgeon may disengage the working element for enucleation procedure and engage the working element for morcellation procedure, as shown in FIG. 5. In embodiments, the knob 520 may be used to allow the inner blade 254 to engage in or disengage out the endoscope 211.

Figure 8:
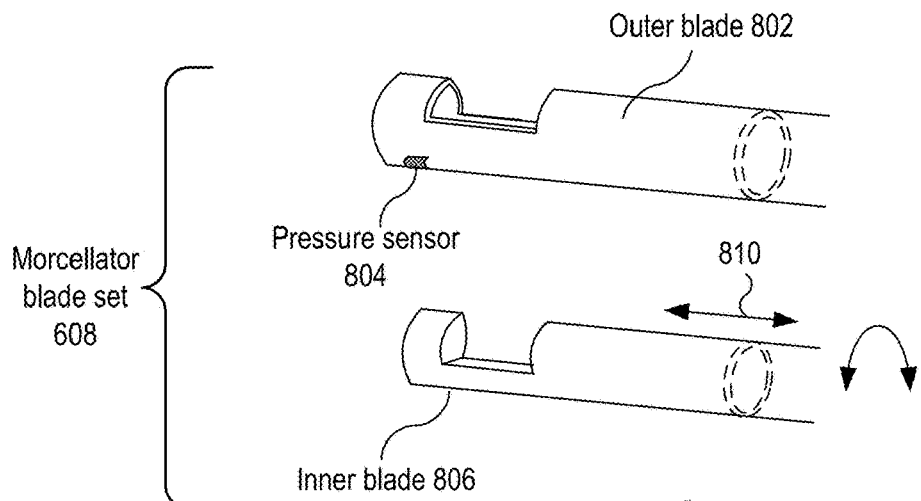
FIG. 8 shows a perspective view of a blade set of a morcellator according to embodiments of the present disclosure.

As discussed above, the surgeon may manipulate the morcellator handpiece 210 to control the reciprocal, oscillating, or rotating motion of the inner blade 254. FIG. 8 shows a perspective view of the morcellator blade set 608 according to embodiments of the present disclosure. As depicted, the morcellator blade set 608 may include an outer blade 802 and an inner blade 806. For the purpose of illustration, in FIG. 8, the inner blade 806 is shown to be dissembled from the outer blade 802, even though the inner blade 806 is inserted into the outer blade 802 during morcellation procedure and it may reciprocate relative to the outer blade 802 along the axial direction 810. In embodiments, other types of morcellator blade sets may be used in place of the morcellator blade set 608. For instance, the inner blade 806 may rotate relative to the outer blade 802. In FIG. 2, the inner blade 254 may correspond to the inner blade 806 in FIG. 8, i.e., the distal end of the inner blade 806 is located inside the bladder 204 and the proximal end of the inner blade is located near the morcellator handpiece 210.

Figure 9A:
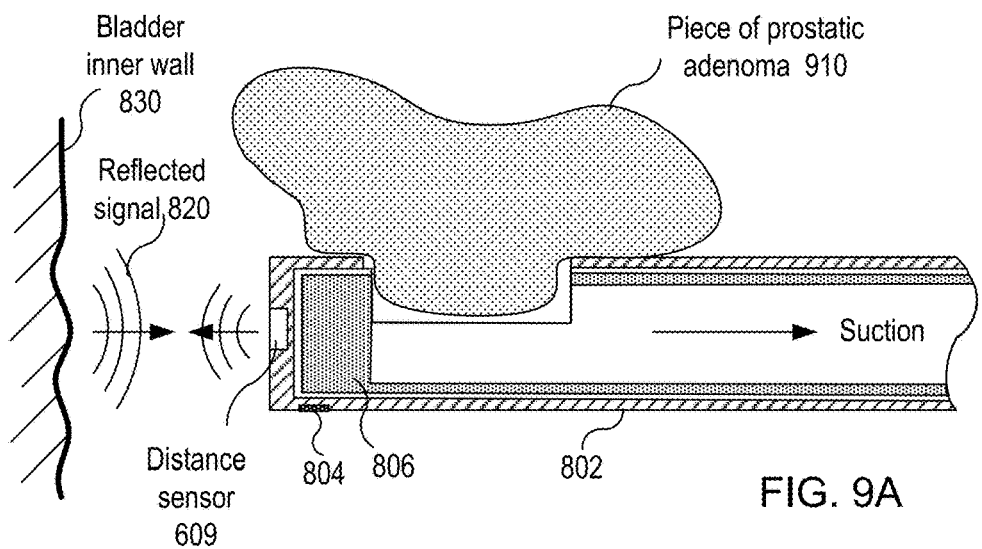
FIG. 9A shows a cross sectional view of the blade set of the morcellator in FIG. 8 according to embodiments of the present disclosure.
Figure 9B:
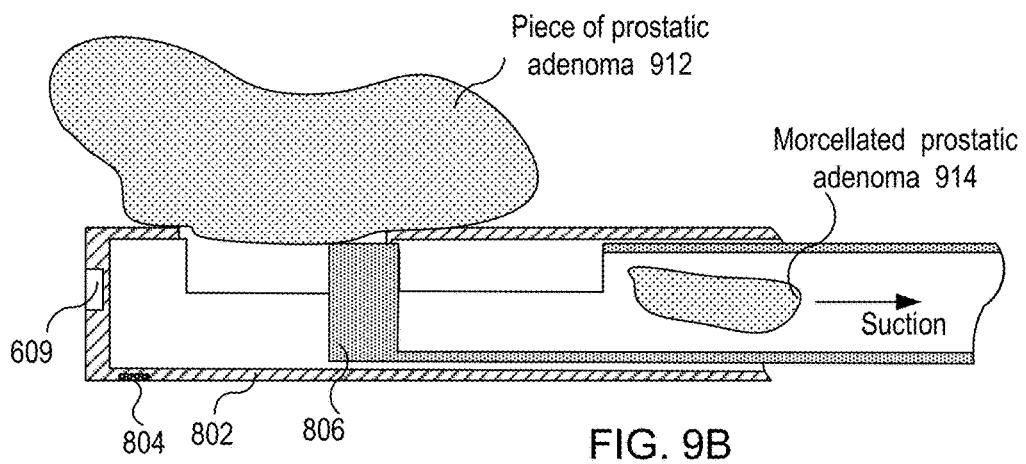
FIG. 9B shows a cross sectional view of the blade set of the morcellator in FIG. 8 according to embodiments of the present disclosure.

FIGS. 9A and 9B shows cross sectional views of the morcellator blade set 608 according to embodiments of the present disclosure. As depicted in FIG. 9A, suction may be provided to the inner blade 806 so that a portion of the large piece of prostatic adenoma (or shortly piece of tissue) 910 may be engaged into the inner blade 806. Then, as depicted in FIG. 9B, the inner blade 806 may slide relative to the outer blade 802, cutting the engaged portion of the piece of tissue 910 into a small piece of tissue 914. The small piece of morcellated adenomatous tissue 914 of the prostate may travel through the inner blade 806 to the flexible tube 250. In embodiments, the inner blade 806 may repeat the steps described in FIGS. 9A and 9B, fragmenting the remaining piece of tissue 912 into smaller pieces of tissue. In embodiments, the fluid inside the bladder 204 may sucked through the inner blade 806 to the flexible tube 250 along with the smaller morcellated pieces of tissue 914 and exit the flexible tube 250, as indicated by the arrow 273.

In embodiments, the outer blade 802 may include a distance sensor 609 that measures the distance between the end of the outer blade 802 and the inner wall 830 of the bladder 204. In embodiments, the distance sensor 609 may send a signal toward the inner wall 830, detect the signal 820 reflected from the inner wall 830 of the bladder, measure the time-of-flight of the signal and send the measured time-of-flight to the device 224. Then, based on the time of flight of the signal, the signal processor 308 may determine the distance between the end of the outer blade 802 and the inner wall 830 of the bladder. In embodiments, if the distance is shorter than a preset safe distance, the signal processor 308 may send an audio warning signal through the speaker 312 and/or display a visual warning signal on the display 226.

In embodiments, the distance sensor 609 may include a signal generator for generating any suitable type of signal, such as ultrasound, infra-red light, radio signal, visible light, so on. In embodiments, the distance sensor 609 may also include a signal detector for detecting the reflected signal 820.

In embodiments, as discussed above, a pressure sensor 804 may be installed on the outer blade 802 and measure the pressure inside the bladder. In FIG. 8, the pressure sensor 804 is shown to be located on the side wall of the outer blade 802. However, it should be apparent to those of ordinary skill in the art that the pressure sensor 804 may be located in other suitable location near the distal end of the outer blade 802, such as a location right next to the distance sensor 609.

Figure 10:
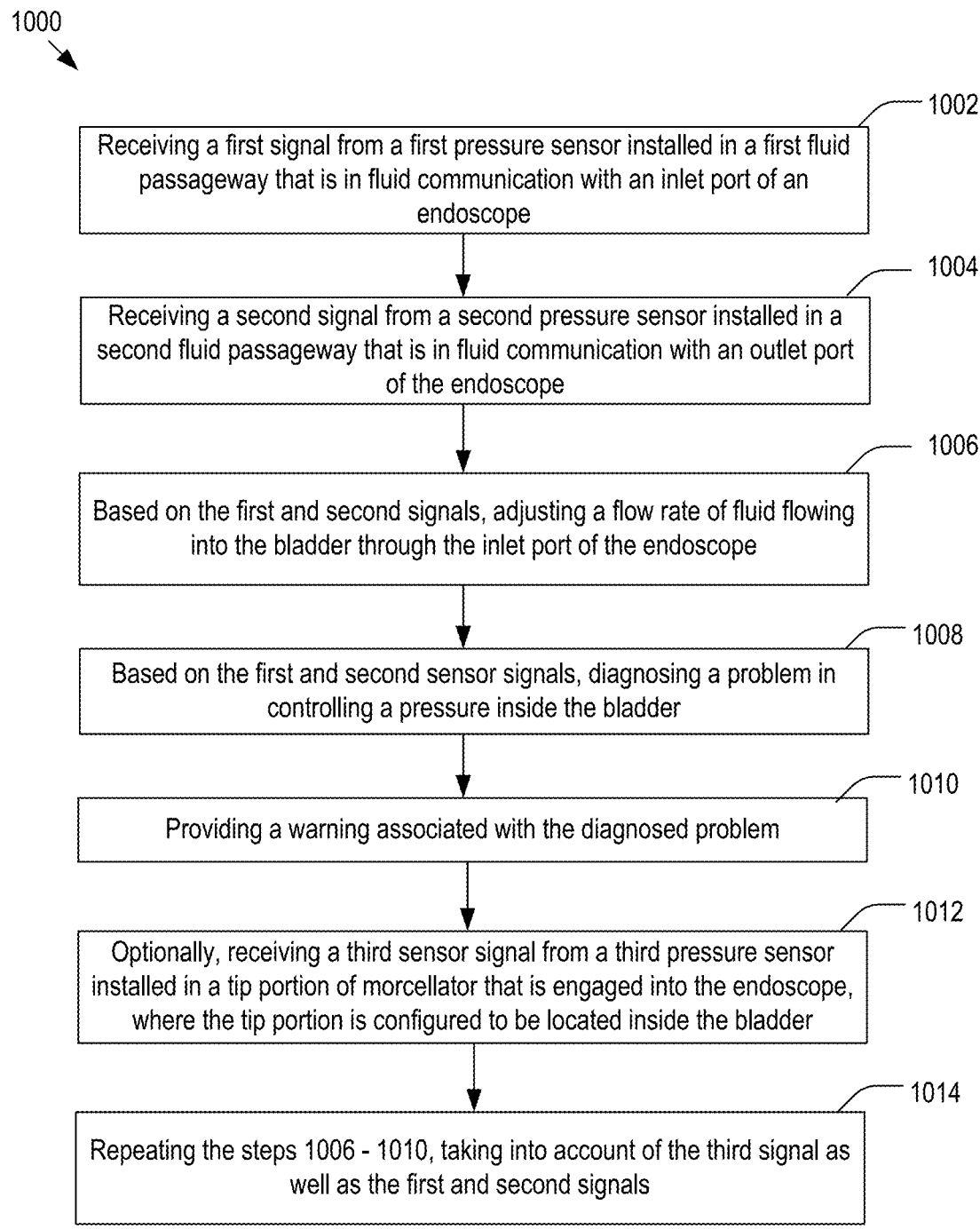
FIG. 10 shows a flowchart of an exemplary process for controlling a bladder pressure according to embodiments of the present disclosure.

As discussed above, in embodiments, the monitoring of the bladder may be performed to ensure that the bladder 204 remains fully distended during the morcellation procedure. Since the variation in the bladder volume is closely related to the change in the pressure of the fluid inside and outside the bladder 204, in embodiments, the pressure of the fluid may be measured at various locations. FIG. 10 shows a flowchart 1000 of an exemplary process for controlling the bladder pressure according to embodiments of the present invention. At step 1002, the device 224 may receive a first signal from the inflow-side pressure sensor 215 installed in the inflow tube 213 that forms a passageway of fluid flowing into the bladder 204. In embodiments, the inflow tube 213 may be in fluid communication with an inlet port (such as inflow stopcock 506) of the endoscope. In embodiments, the inflow-side pressure sensor 215 may measure the pressure of the fluid entering the bladder 204. At step 1004, the device 244 may also receive a second signal from the outflow-side pressure sensor 219 installed in the drain tube 221 that is in fluid communication with an outlet port (such as the outflow stopcock 504) of the endoscope 211. In embodiments, the outflow valve 217 may be closed during the morcellation procedure while the drain tube 221 may remain in fluid communication with the outlet port of the endoscope 211. As such, during the morcellation procedure, the pressure measured by the second pressure sensor 219 may indicate the pressure inside the bladder 204.

At step 1006, based on the first and second signals, the device 224 may adjust a flow rate of fluid flowing into the bladder through the inlet port of the endoscope. In embodiments, the device 224 may move the servo mechanism 292 in the vertical direction to thereby adjust the hydraulic head of the fluid in the irrigation fluid container 216. In embodiments, the pump 293 may be operated to inject fluid into the inflow tube 213. At step 1008, based on the first and second signals, the device 224 may diagnose a problem in controlling the pressure inside the bladder 204. For instance, if the pressure measured by the inflow-side sensor 215 is within an acceptable range and the pressure measured by the outflow-side sensor 219 is below an acceptable range, the device 224 may conclude that the outflow valve 217 is open.

At step 1010, the device 224 may issue a warning signal associated with the diagnosed problem to the surgeon. In embodiments, the speaker 312 may provide an audio warning signal to the surgeon. In embodiments, the display 226 may provide a visual warning signal to the surgeon. Optionally, at step 1012, the device 224 may receive a third sensor signal from the pressure sensor 804 installed in the tip portion of the morcellator device (more specifically, outer blade 802), where the tip portion is located inside the bladder 204. At step 1014, the device 224 may repeat the steps 1006-1010, taking into account the third signal as well as the first and second signals.

As depicted in FIGS. 2-10, one or more of the pressure sensors 215, 219, and 804, distance sensor 609, image processor 306, and flow meter 214 may form a feedback system to control the pressure inside the bladder. Also, signals from one or more these components may be considered to diagnose the system 200. FIG. 11 shows a diagnosis table 1100 according to embodiments of the present invention. In the table 1100, diagnosis results for four scenarios are considered only, even though other scenarios may occur in the system 200. By way of example, in the third scenario, both of the inflow-side pressure sensor 215 and the outflow-side pressure sensor 219 shows low fluid pressure (for example, less than 20 cmH2O), the distance sensor 609 shows that the bladder wall is near the tip of the morcellator (for example, less than 3 cm apart), the volume of the bladder based on the ultrasound image 230 is less than 200 ml, and the flow meter 214 shows that the flow rate is normal, which indicates that the bladder is collapsed due to excessive outflow secondary to inadvertently open outflow and/or excessive suctioning-out. In this third scenario, based on one or more of the signals from these six sensors, the processor 302 may conclude that there is an excessive outflow and give a warning signal to the surgeon so that the surgeon may check both the outflow stopcock 504 and the outflow valve 217, or so that the surgeon may wait until the bladder is completely filled again. In embodiments, for other scenarios, the computing device 224 (or, the processor 302) may issue a warning signal that corresponds to the diagnosis result in the bottom row of the table 1100 and/or actuate one or more components in the system 200 to resolve the issue associated with the diagnosis result.

It is noted that the various threshold values in FIG. 11 may vary depending on the patient's normal bladder volume and pressure. For instance, the bladder may be considered full when the volume of the bladder is over 450 ml (instead of 500 ml) and the bladder may be considered collapsed if the bladder volume is less than 150 ml (instead of 200 ml). In another example, the pressure measured by the sensor 804 at the morcellator tip may be considered high when the measured pressure is over 55 cm H2O and the pressure may be considered low when the measured pressure is less than 15 cm H2O.

Figure 12:
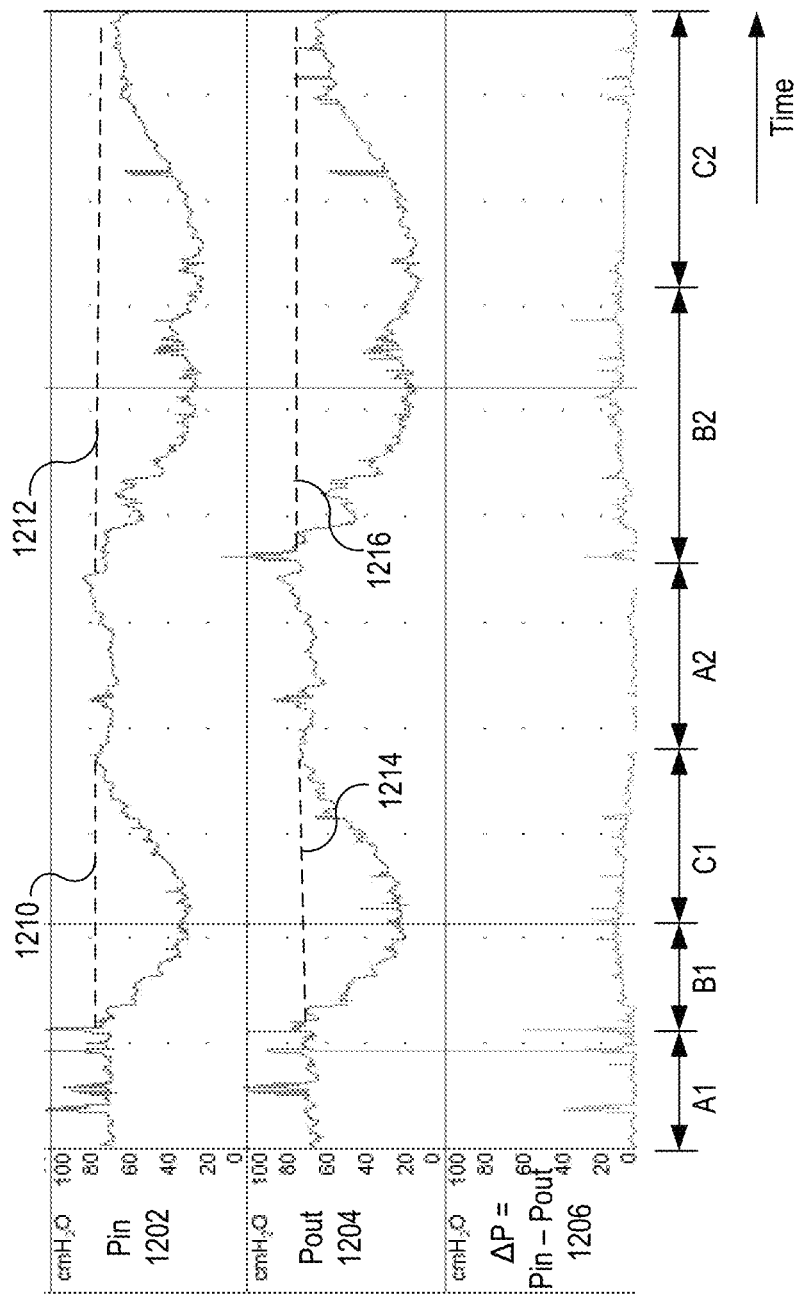
FIG. 12 shows exemplary plots of pressure as a function of time according to embodiments of the present disclosure.

FIG. 12 shows exemplary plots of pressure as a function of time according to embodiments of the present disclosure. In FIG. 12, the plots 1202, 1204 and 1206 represent the pressure, Pin, measured by the inflow-side pressure sensor 215, the pressure, Pout, measured by the outflow-side pressure sensor 219, and the difference between Pin and Pout during operation, respectively. For the purpose of illustration, the pressures in FIG. 12 are measured while the irrigation fluid container 216 is fixed in space, i.e., the hydraulic head of the fluid in the irrigation fluid container 216 is not controlled by the computing device 224 during operation.

During the steady state, A1, the bladder is fully distended and the pressures remain at steady levels. During the morcellation procedure B1, the rate of outflow exiting the bladder through the inner blade 806 of the morcellation blade set 608 may be higher than the rate of inflow entering the bladder and as such, the pressures Pin and Pout may decrease gradually. At the end of the morcellation procedure, the bladder collapses and the pressures, Pin and Pout, fall below threshold levels. Then, the surgeon may stop the morcellation procedure and wait until the bladder is fully distended again during the waiting (refilling) period C1 and reach a steady state A2. At the end of the steady state A2, the surgeon may resume the morcellation procedure during the time period B2. When the bladder collapses at the end of the time period B2, the surgeon may wait until the bladder is fully distended again during the waiting period C2. As the surgeon performs the morcellation procedure, the plots of the pressure 1202, 1204, and 1206 may have a repeated pattern that is similar to the pattern including the time periods A2, B2 and C2.

In embodiments, during the morcellation procedure B1 (and B2), the computing device 224 may move the servo mechanism 292 in the vertical direction, to thereby adjust the hydraulic head of the fluid in the irrigation fluid container 216. For instance, the servo mechanism 292 may be moved upward so that the flow rate into the bladder may be increased and the pressures Pin and Pout may not decrease as shown in FIG. 12. In such a case, the pressures Pin and Pout during the morcellation procedure may remain the same as in the steady state A1 (and A2) and the bladder remains fully distended. Also, the surgeon may not need to stop and wait until the bladder is fully distended again during the period C1 (and C2). The broken lines 1210-1216 represent the pressures that are measured while the servo mechanism 292 is controlled by the computing device 224 to move along the vertical direction during operation so that the rate of low into the bladder is controlled. As indicated by the broken lines 1210-1216, during the morcellation procedure, the pressures Pin and Pout remain the same as in the steady state and the bladder remains distended, and as such, there is not waiting period.

In embodiments, if the bladder collapses and/or the pressure Pin (and/or Pout) falls below thresholds, the computing device 204 may issue a warning sign so that the surgeon may stop the morcellation procedure right away.

In embodiments, one or more computing system may be configured to perform one or more of the methods, functions, and/or operations presented herein. Systems that implement at least one or more of the methods, functions, and/or operations described herein may comprise an application or applications operating on at least one computing system. The computing system may comprise one or more computers and one or more databases. The computer system may be a single system, a distributed system, a cloud-based computer system, or a combination thereof.

It shall be noted that the present disclosure may be implemented in any instruction-execution/computing device or system capable of processing data, including, without limitation laptop computers, desktop computers, and servers. The present invention may also be implemented into other computing devices and systems. Furthermore, aspects of the present invention may be implemented in a wide variety of ways including software (including firmware), hardware, or combinations thereof. For example, the functions to practice various aspects of the present invention may be performed by components that are implemented in a wide variety of ways including discrete logic components, one or more application specific integrated circuits (ASICs), and/or program-controlled processors. It shall be noted that the manner in which these items are implemented is not critical to the present invention.

Figure 13:
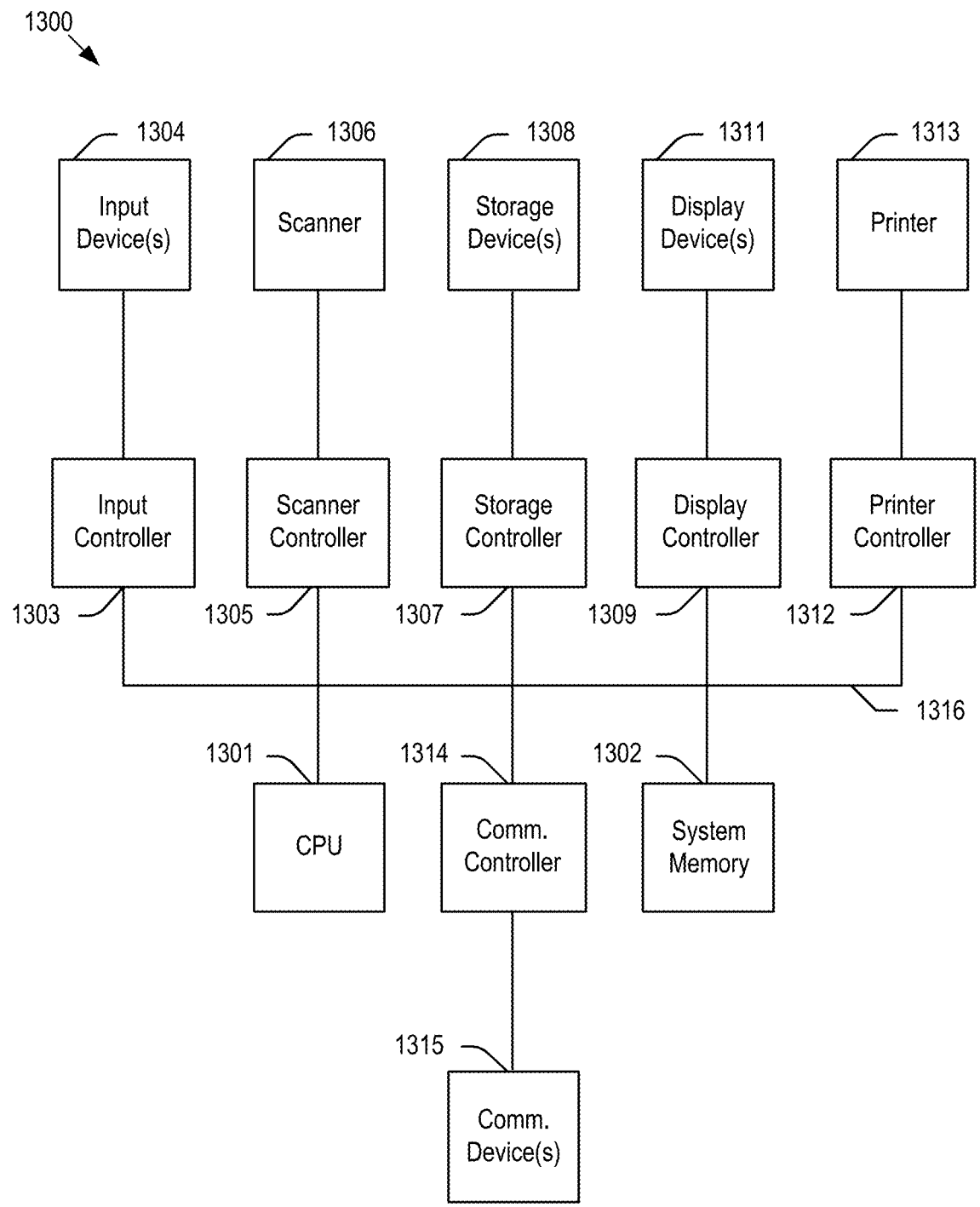
FIG. 13 shows a computer system according to embodiments of the present disclosure.

Having described the details of the invention, an exemplary system 1300, which may be used to implement one or more aspects of the present invention, will now be described with reference to FIG. 13. The computing system 224 in FIG. 2 may include one or more components in the system 1300. As illustrated in FIG. 13, system 1300 includes a central processing unit (CPU) 1301 that provides computing resources and controls the computer. CPU 1301 may be implemented with a microprocessor or the like, and may also include a graphics processor and/or a floating point coprocessor for mathematical computations. System 1300 may also include a system memory 1302, which may be in the form of random-access memory (RAM) and read-only memory (ROM).

A number of controllers and peripheral devices may also be provided, as shown in FIG. 13. An input controller 1303 represents an interface to various input device(s) 1304, such as a keyboard, mouse, or stylus. There may also be a scanner controller 1305, which communicates with a scanner 1306. System 1300 may also include a storage controller 1307 for interfacing with one or more storage devices 1308 each of which includes a storage medium such as magnetic tape or disk, or an optical medium that might be used to record programs of instructions for operating systems, utilities and applications which may include embodiments of programs that implement various aspects of the present invention. Storage device(s) 1308 may also be used to store processed data or data to be processed in accordance with the invention. System 1300 may also include a display controller 1309 for providing an interface to a display device 1311, which may be a cathode ray tube (CRT), a thin film transistor (TFT) display, or other type of display. System 1300 may also include a printer controller 1312 for communicating with a printer 1313. A communications controller 1314 may interface with one or more communication devices 1315, which enables system 1300 to connect to remote devices through any of a variety of networks including the Internet, an Ethernet cloud, an FCoE/DCB cloud, a local area network (LAN), a wide area network (WAN), a storage area network (SAN) or through any suitable electromagnetic carrier signals including infrared signals.

In the illustrated system, all major system components may connect to a bus 1316, which may represent more than one physical bus. However, various system components may or may not be in physical proximity to one another. For example, input data and/or output data may be remotely transmitted from one physical location to another. In addition, programs that implement various aspects of this invention may be accessed from a remote location (e.g., a server) over a network. Such data and/or programs may be conveyed through any of a variety of machine-readable medium including, but are not limited to: magnetic media such as hard disks, floppy disks, and magnetic tape; optical media such as CD-ROMs and holographic devices; magneto-optical media; and hardware devices that are specially configured to store or to store and execute program code, such as application specific integrated circuits (ASICs), programmable logic devices (PLDs), flash memory devices, and ROM and RAM devices.

Embodiments of the present invention may be encoded upon one or more non-transitory computer-readable media with instructions for one or more processors or processing units to cause steps to be performed. It shall be noted that the one or more non-transitory computer-readable media shall include volatile and non-volatile memory. It shall be noted that alternative implementations are possible, including a hardware implementation or a software/hardware implementation. Hardware-implemented functions may be realized using ASIC(s), programmable arrays, digital signal processing circuitry, or the like. Accordingly, the "means" terms in any claims are intended to cover both software and hardware implementations. Similarly, the term "computer-readable medium or media" as used herein includes software and/or hardware having a program of instructions embodied thereon, or a combination thereof. With these implementation alternatives in mind, it is to be understood that the figures and accompanying description provide the functional information one skilled in the art would require to write program code (i.e., software) and/or to fabricate circuits (i.e., hardware) to perform the processing required.

It shall be noted that embodiments of the present invention may further relate to computer products with a non-transitory, tangible computer-readable medium that have computer code thereon for performing various computer-implemented operations. The media and computer code may be those specially designed and constructed for the purposes of the present invention, or they may be of the kind known or available to those having skill in the relevant arts. Examples of tangible computer-readable media include, but are not limited to: magnetic media such as hard disks, floppy disks, and magnetic tape; optical media such as CD-ROMs and holographic devices; magneto-optical media; and hardware devices that are specially configured to store or to store and execute program code, such as application specific integrated circuits (ASICs), programmable logic devices (PLDs), flash memory devices, and ROM and RAM devices. Examples of computer code include machine code, such as produced by a compiler, and files containing higher level code that are executed by a computer using an interpreter. Embodiments of the present invention may be implemented in whole or in part as machine-executable instructions that may be in program modules that are executed by a processing device. Examples of program modules include libraries, programs, routines, objects, components, and data structures. In distributed computing environments, program modules may be physically located in settings that are local, remote, or both.

One skilled in the art will recognize no computing system or programming language is critical to the practice of the present invention. One skilled in the art will also recognize that a number of the elements described above may be physically and/or functionally separated into sub-modules or combined together.

It will be appreciated to those skilled in the art that the preceding examples and embodiment are exemplary and not limiting to the scope of the present invention. It is intended that all permutations, enhancements, equivalents, combinations, and improvements thereto that are apparent to those skilled in the art upon a reading of the specification and a study of the drawings are included within the true spirit and scope of the present invention.

What is claimed is:

1. A system for monitoring a volume of a bladder during a surgical procedure, comprising:
   one or more processors; and
   a memory that is communicatively coupled to the one or more processors and stores one or more sequences of instructions, which when executed by one or more processors causes steps to be performed comprising:
      receiving information of a maximum volume of the bladder before a surgical procedure;
      receiving one or more ultrasound images of the bladder;
      based on the one or more ultrasound images, determining a volume of the bladder;
      comparing a maximum volume of the bladder to the determined volume of the bladder; and
      responsive to a difference between the maximum volume and determine volume of the bladder exceeding a threshold, issuing a warning associated with the difference.

2. The system of claim 1, wherein the memory further stores one or more sequences of instructions, when executed by the one or more processors, causes steps to be performed comprising:
   displaying the determined volume of the bladder on a display screen.

3. The system of claim 1, wherein the memory further stores one or more sequences of instructions, when executed by the one or more processors, causes steps to be performed comprising:
   identifying a tip portion of a morcellator and an inner wall of the bladder in the one or more ultrasound images, the tip of the morcellator being configured to be located inside the bladder during the surgical procedure;

determining a distance between the tip of the morcellator and the inner wall of the bladder; and responsive to the distance being less than a minimum safety value, issuing a warning of the determined distance.

4. The system of claim 1, wherein the memory further stores one or more sequences of instructions, when executed by the one or more processors, causes steps to be performed comprising:

identifying a tip portion of a morcellator and an inner wall of the bladder in the one or more ultrasound images, the tip of the morcellator being configured to be located inside the bladder during the surgical procedure; and tracing a location of the tip portion during the surgical procedure.

* * * * *